United States Patent [19]
Craig

[11] Patent Number: 5,988,703
[45] Date of Patent: Nov. 23, 1999

[54] FLUID CONNECTOR SYSTEM FOR A PLANAR MANIFOLD ASSEMBLY

[75] Inventor: Stephen R. Craig, Wilmington, Del.

[73] Assignee: Hewlett-Packard Company, Palo Alto, Calif.

[21] Appl. No.: 08/903,843

[22] Filed: Jul. 31, 1997

[51] Int. Cl.$^6$ ..................................................... F16L 13/02
[52] U.S. Cl. .................................. 285/288.1; 285/124.1; 285/136.1; 219/93
[58] Field of Search ............................. 285/288.1, 124.1, 285/21.1, 136.1; 219/93

[56] References Cited

U.S. PATENT DOCUMENTS

| | | | |
|---|---|---|---|
| 2,202,405 | 5/1940 | Smith | 285/288.1 X |
| 2,257,427 | 9/1941 | Parker | 285/288.1 X |
| 2,360,660 | 10/1944 | Eaton et al. | 219/93 |
| 2,903,562 | 9/1959 | Emmons et al. | 219/93 |
| 4,480,166 | 10/1984 | Leech | 219/93 |
| 4,677,271 | 6/1987 | Opprecht | 219/93 |
| 4,901,135 | 2/1990 | Costigan | 219/93 |
| 5,039,844 | 8/1991 | Nagahori | 219/93 |
| 5,567,868 | 10/1996 | Craig et al. | |

*Primary Examiner*—Dave W. Arola
*Attorney, Agent, or Firm*—Mark Z. Dudley

[57] ABSTRACT

A fluid connector system for connecting a conduit having a fluid-bearing capability to a channel having a fluid-bearing capability in a planar manifold assembly, thereby providing a substantially leak-free fluid communication between the conduit and the channel. A preferred embodiment of the fluid connector system is effective for connecting a conduit to a planar manifold situated in a sample analysis system. The conduit is located in a fluid-handling functional device and communicates with a device port located in a port surface region on the fluid handling functional device. Located within the port surface region, and encircling the first port, is a weld projection. The channel is located in a receiver portion of a planar assembly and communicates with a manifold port. A port surface region on the exterior of the planar assembly encompasses the manifold port. The port surface regions are complementary in that they may be superimposed so as to co-locate the device port and the manifold port. The leading edge may contact the port surface region on the planar manifold in a fashion that defines a line of contact. The weld projection and the material that underlies the line of contact are both formed of electrically resistive material suited to melting and subsequent fusion via resistive heating due to a brief application of an electric current. Accordingly, upon application of a current pulse that is sufficient to cause resistive heating at the weld projection, the weld projection and the material that underlies the line of contact are heated and intermixed, thereby becoming fused together. Upon cooling, the weld projection and the line of contact are merged and thus nearly indistinguishable, thus fixing the port surface regions together such that a hermetic seal is imposed about the juncture of the superimposed device port and manifold port.

7 Claims, 9 Drawing Sheets

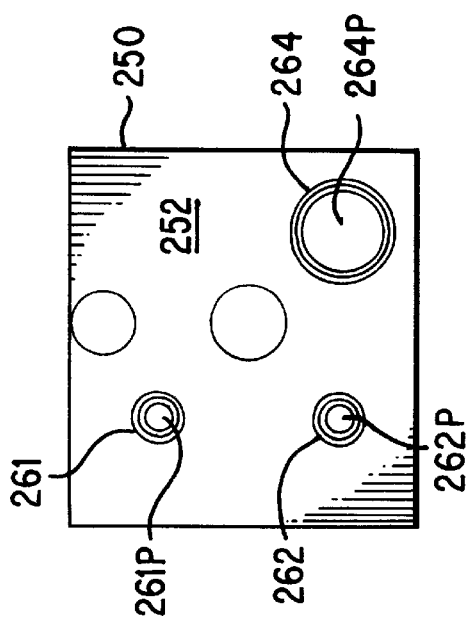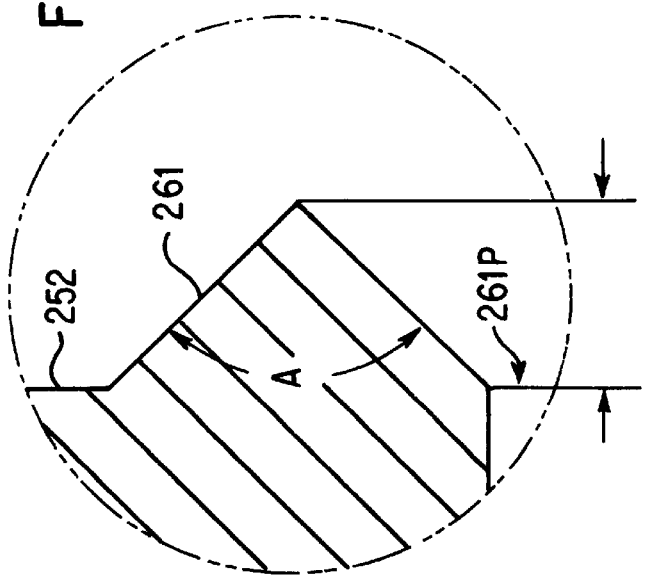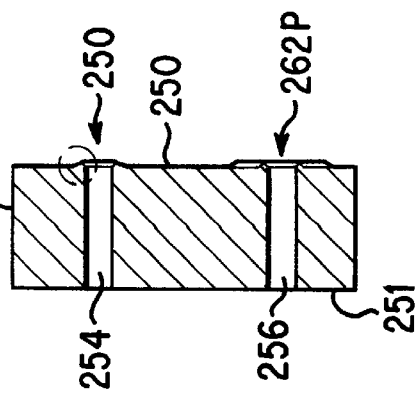

FLUID CONNECTOR SYSTEM FOR A PLANAR MANIFOLD ASSEMBLY

FIELD OF THE INVENTION

The present invention relates to methods and apparatus for effecting fluid connections of fluid flow in an analytical instrument, and more particularly with a fluid connector system for use in apparatus such as a planar manifold assembly in an analytical instrument.

BACKGROUND OF THE INVENTION

Analytical instruments which rely upon regulated fluid flow are commonly employed in a wide variety of applications, such as sample purification, chemical analysis, clinical assay, and industrial processing. For many instruments, an extensive and complex array of tubing, fittings and connectors are employed to provide the many flow paths that are necessary for optimum operation, and to effect the attachment of sensors, valves, and the like.

Such instruments typically function with use of devices that initiate, maintain, halt, or reverse a flow stream through the device. This may be accomplished by combinations of valves and/or pumps. Very often, such instruments devices require a complex arrangement of multiple flow paths to operate efficiently. Generally, efficient operation requires a flow system combining flow-through components, such as sorbent columns and connective tubing, with terminal components, such as needles, pumps, and drains. Different flow paths are frequently required to, for example, isolate a component from the flow system, include a component into the flow system, or rearrange the order of the components in the flow system. Further, there is the need to sense certain characteristics of the fluid flow at differing points in the flow paths. Examples of such sensed characteristics include the pressure, flow rate, and temperature of the fluid. Other characteristics related to the particular fluid flow include the presence or absence of a fluid component, such as an analyte or contaminant. Such needs are typically addressed by the use of fluid connectors for attachment of differing, plural sensors.

Combinations of fluid connectors are typically necessary to provide flow paths among the flow-through components and terminal components employed in a flow system.

There exists the practical problem, therefore, of connecting the valves, sensors, fittings, and the like that are required for the multitude of flow path combinations in a modern analytical instrument. Hence, another practical problem remains in connecting quite a large number of devices in a multitude of flow path combinations in an instrument. The complexity of such systems introduces reliability concerns. Because the devices that are implemented in these flow systems are sometimes automated, the reliability and accessibility of the pneumatic connection are features critical to successful instrument operation.

Another problem involves the proper orientation of all of the valves, sensors, and the like so as to allow the desired combinations of flow paths, yet also provide an assembly that is compact, easily-manufactured, inexpensive, and reliable. For example, the provision of fluid-tight connections in a complex fluid-handling assembly has become exceedingly problematic as the assembly is reduced in size.

Gas and liquid chromatographs are particular examples of an instrument having a fluid flow system wherein certain characteristics related to a particular fluid flow are detected, e.g., the presence or absence of a fluid component, such as an analyte or contaminant. Some gas chromatographs employ fluids in the form of combustible gasses in performing an analysis. Even though the pneumatic fittings in the typical chromatograph are designed to minimize leakage, one may nonetheless consider a pneumatic fault mode wherein a gas leak could occur and sufficient gas could accumulate so as to pose an unsafe condition.

The instrument may also require a complex array of fluid connections that are specialized (non-standard or require expensive or low volume parts) such that their manufacture is labor- and capital-extensive.

It will also be appreciated that a flow system in an instrument must be versatile, that is, capable of being configured during assembly, or reconfigured to meet the requirements of a particular application as additional valves, fittings, etc. are added to the flow system.

In response to these problems, U.S. Pat. No. 5,567,868, issued to Craig et al., disclosed an analytical instrument, preferably in the form of a chromatograph, that includes a computer, a pneumatic controller responsive to the computer, and planar manifold assembly. The planar manifold assembly includes one or more fluid-handling functional devices attached to a planar manifold. Multiple fluid-handling functional devices may then be coordinated and assembled so as to connect to pneumatic channels that are integrated in the planar manifold, and thus many of the fluid flow paths are integral to the planar manifold, which is itself quite compact and amenable to construction in a variety of shapes and configurations. The advantages of the planar manifold assembly include the reduction of external connections between fluid-handling functional devices (such as fittings, valves, sensors, and the like) by use of a single planar manifold for the provision of a plurality of flow paths. The fluid-handling functional devices that connect to the planar manifold are constructed to be surface-mounted to offer reliable, fluid-tight connection without the complexity and difficulty of previously-known pneumatic connections.

Nonetheless, there still remains a difficulty in effecting such fluid connections between one or more channels in the planar manifold and a corresponding channel or conduit in one of the great variety of differing devices, tubes, fittings, and the like that are attractive for use with the planar manifold assembly. A significant disadvantage of presently known connectors is that they have a dead space communicating with the ends of the fluid channels being coupled. A portion of the fluid emerging from the end of one channel quickly finds its way into the dead space but a relatively long time is required for it to enter the other channel. For example, in a tube connected by conventional means to a detector in a chromatograph, the concentration of a sample fluid emerging from one end of the tube can increase rapidly to a maximum value and then slowly decay to zero so as to cause a phenomenon known as tailing. As those skilled in the art are aware, this can make it difficult to detect separate components of the sample.

Another significant disadvantage of presently known fluid connector devices is that the fluid flowing through a fluid connector device can be degraded by contact with large areas of less-than-inert surfaces of the device.

Another significant disadvantage of presently known fluid connector devices is that many fluid handling devices, and the planar assembly itself, are becoming even smaller and are designed to be assembled in a compact, densely-populated arrangement. Conventional fluid connectors, in contrast, remain undesirably large and bulky.

There is accordingly a need in many applications for a fluid connector system for use in effecting a pneumatic connection to a channel in a planar manifold assembly or similar planar device in an analytical instrument, wherein such a system would offer such attributes as: miniaturization, reliability, simplicity, robust, ease in assembly and maintenance, and low cost.

SUMMARY OF THE INVENTION

The present invention provides a fluid connector system for connecting a conduit having a fluid-bearing capability to a channel located in a planar manifold assembly and having a fluid-bearing capability, thereby providing means for effecting a substantially leak-free fluid communication between the conduit and the channel.

A preferred embodiment of a fluid connector system constructed according to the present invention may be employed for connecting a conduit located in a fluid-handling functional device to a channel located in a planar manifold. The conduit communicates with a device port located in a device port surface region on the fluid handling functional device. Located within the device port surface region, and encircling the device port, is a weld projection. The channel is located in a receiving portion of a planar assembly and communicates with a manifold port. A manifold port surface region on the exterior of the planar assembly encompasses the manifold port. The device port surface region and the manifold port surface regions are complementary in that they may be superimposed so as to co-locate the device port and the manifold port. Locating means may optionally be employed to aid such co-location.

The leading edge of the weld projection is adapted for contact with the planar manifold as the device port surface region is urged against the manifold port surface region by a biasing force. The leading edge of the weld projection contacts the manifold port surface region on the planar manifold in a fashion that defines a line of contact. The weld projection and the material that underlies the line of contact are both formed of electrically resistive material suited to melting and subsequent fusion via resistive heating due to a brief application of an electric current. Accordingly, upon application of a current pulse that flows between the weld projection and the manifold port surface region, the current density of the pulse is concentrated at the line of contact and is sufficient to cause resistive heating of the weld projection and the material that underlies the line of contact. The weld projection and the material that underlies the line of contact are heated and intermixed, thereby becoming fused together. Upon cooling, the manifold port surface region and the device port surface region are found to be superimposed, and the weld projection and the line of contact are merged and thus no longer distinguishable, thus fixing the device port surface region and the manifold port surface region together such that a hermetic seal is imposed at the juncture of the superimposed device port and manifold port.

In an alternative embodiment, the weld projection may be located on the manifold port surface region, and thus encircle the manifold port, instead of being located about the device port. Accordingly, the present invention is directed to deployment of at least one weld projection located about a respective port on at least one of the manifold port surface region and the device port surface region. In the spirit of the invention, either embodiment is effective for producing a robust, permanent, and hermetic fluid seal between the channel and the conduit.

A preferred method for coupling the conduit to the channel situated in the receiver portion includes a) mounting the device port surface region onto the manifold port surface region to engage the leading edge of the weld projection against the manifold port surface region and to superimpose the device port and the manifold port; b) urging the device and the planar manifold together to cause a line contact of the manifold port surface region by the leading edge of the weld projection; c) subjecting the port surface regions to a current flow therebetween sufficient to cause localized, intense heating at the leading edge of the projection weld and at the line of contact.

Preferably, the weld projection is provided in an annular or similar closed geometric form when viewed from above, such that the desired configuration of the line contact will provide a complete seal about the device port and the manifold port.

Another embodiment of a fluid connector is preferably constructed as an upright fluid connector for connecting tubing, sleeving, fittings and the like to a planar manifold. The fluid connector thus may be employed to effect leak-free transfer of of a sample fluid carried in, for example, a capillary tube, to the channel. The upright connector includes a upper fitting shaped as a tube and an attached lower fitting shaped as a disk-like platform. The upper fitting extends from a center portion of the topside of the lower fitting. At the underside of the platform is a lower port and at the opposing ends of the connector, at the mouth of the upper fitting, is an upper port. An internal bore provides fluid communication between the upper and lower ports. Encircling the lower port is a downwardly-extending weld projection. Upon deploying the weld projection against the manifold port surface region while the manifold port and the lower port are superimposed, and by application of a current pulse as described hereinabove, the weld projection and the line of contact are subject to resistive heating and merge to be nearly indistinguishable, thus fixing the underside of the platform to the planar manifold such that a hermetic seal is imposed about the juncture of the superimposed lower port and manifold port.

Still another embodiment of an upright fluid connector constructed in accordance with this invention includes a rigid body having upper and lower fittings, a cavity in the upper fitting, and a central bore extending between an upper port in the cavity and a lower port in the underside of the lower fitting. An internal bore provides fluid communication between the upper and lower ports. The lower port is encircled by a downwardly extending weld projection. Upon deploying the weld projection against the manifold port surface region while the manifold port and the lower port are superimposed, and by application of a current pulse as described hereinabove, the weld projection and the line of contact are subject to resistive heating and merge to be nearly indistinguishable, thus fixing the underside of the lower fitting to the planar manifold such that a hermetic seal is imposed about the juncture of the superimposed lower port and manifold port. A tubing member may then be easily coupled to the internal bore by use of sealing means such as a tapered ferrule having an axial passageway that is aligned with and mounted on the end of the tubing to which a connection is to be made, and by use of compression means such as a nut that is rotated in threaded engagement with the upper fitting so as to force the ferrule and the end of the tubing into the cavity. The relative shapes and dimensions of the cavity and the ferrule are such that as the ferrule is forced into the cavity it is subjected to radial compression so as to attain a gas-tight seal with the exterior surfaces of the tube and the cavity. The interior of the tubing is thereby put in fluid communication with the central bore and the manifold port.

The advantages of the invention may be achieved in a planar chromatographic assembly suitable for use in an analytical instrument. The planar chromatographic assembly includes a planar manifold, a heater assembly for establishing a temperature-controlled zone, an injector section, a separation column having inlet and outlet ends attached to selected internal fluid-bearing conduits in the pneumatic manifold and which is located within the temperature-controlled zone, and one or more fluid-handling functional devices attached to the pneumatic manifold. Manifold ports are provided to offer fluid communication with respective etched channels in the planar manifold. Each fluid-handling functional device includes one or more device ports each encircled by a weld projection amenable to hermetic sealing with a respective interface adjacent a manifold port. (Alternatively, each manifold port may be encircled by a weld projection amenable to hermetic sealing with a fluid handling functional device at a respective device port.) Certain ones of the fluid-handling functional devices may be surface-mounted to thereby establish fluid communication with respective manifold ports. Certain other ones of the fluid-handling functional devices may be connected to the planar manifold using an upright fluid connector so as to thereby establish fluid communication with respective manifold ports.

The contemplated embodiments of a fluid connector are amenable to effect fluid coupling between a planar manifold and a variety of fluid-handling functional devices, including: a) passive devices such as a fluid coupler or a vent for coupling a fluid stream to or from a selected fluid-bearing conduit; b) active devices such as a valve, a fluid regulator, or a fluid flow input device (connectable to a fluid source) operable in response to a control signal from the control system for controlling fluid flow in one or more selected etched channels in the planar manifold, or c) signal generating devices such as a sensor or detector operable so as to provide sense or detection signal indicative of a characteristic of the fluid flow in an etched channel or in the separation column.

In a first aspect of the present invention, the planar chromatographic assembly is assembled with use of a novel fluid connector system for effecting fluid connections between fluid handling functional devices and a planar manifold. The resulting fluid connections are robust (i.e., the hermetic seal withstands operation in an adverse environment, e.g., an environment subject to rapid temperature changes or vibration), substantially free of dead volume, and offer excellent reliability and a long life.

In another aspect of the present invention, the planar chromatographic assembly is provided in a compact assembly thus enabling its use as a portable unit, or for easy attachment in a confined space with respect to a flow system to be analyzed, thus enabling an analysis of a chemical process in an "on-line", "at-line", or similarly oriented type of chemical process analysis.

In another aspect of the present invention, the planar chromatographic assembly may be configured for effecting fluid connections between a planar manifold and certain fluid handling functional devices that would otherwise be difficult or impractical to connect to the planar manifold. Such conventional components include narrow bore tubing, open capillary separation columns, and the like.

BRIEF DESCRIPTION OF THE DRAWINGS

FIG. 6A is a simplified cross-sectional view of another embodiment of a fluid connector for connecting a surface-mounted fluid-handling device to the planar manifold assembly of FIG. 1, and FIG. 6B illustrates a weld projection integrated into a surface portion of the surface-mounted fluid-handling device, in detailed view for clarity.

FIG. 7 is a simplified plan view of the surface-mounted fluid-handling device of FIGS. 6A–6B.

DETAILED DESCRIPTION OF THE PREFERRED EMBODIMENT

The present invention will find useful application in a variety of analytical systems that benefit from effective connection of one or more fluid streams to a planar manifold assembly.

Certain apparatus and methods of the present invention may be employed in particular to provide initiation, distribution, redirection, termination, control, sensing, and other types of functions (collectively defined herein as fluid-handling functions) with respect to one or more of such fluid streams. Gases are the preferred fluids according to the practice of the present invention, and therefore the following description of the invention will include a description of the arrangement, construction, and operation of certain pneumatic devices, and hence is particularly directed to the control and analysis of a gaseous stream in a gas chromatographic analytical system (hereinafter, a chromatograph). However, for the purposes of the following description, the term "pneumatic" will also be considered to refer to all types of fluids.

It should be understood that the teachings herein are applicable to other analytical instruments, including capillary electrophoresis systems, liquid chromatographs, high-pressure gas chromatographs (HPGC), high pressure liquid chromatographs (HPLC), supercritical fluid chromatographs (SFC), and supercritical fluid extraction (SFE) instruments.

In the Figures and the description to follow, like nomenclature and numeric identifiers will refer to like components; signal lines are drawn schematically by single solid lines; pneumatic flow lines or channels are drawn schematically as double solid lines; and components, lines, or channels in phantom are schematically drawn in dashed lines.

Figure 1:
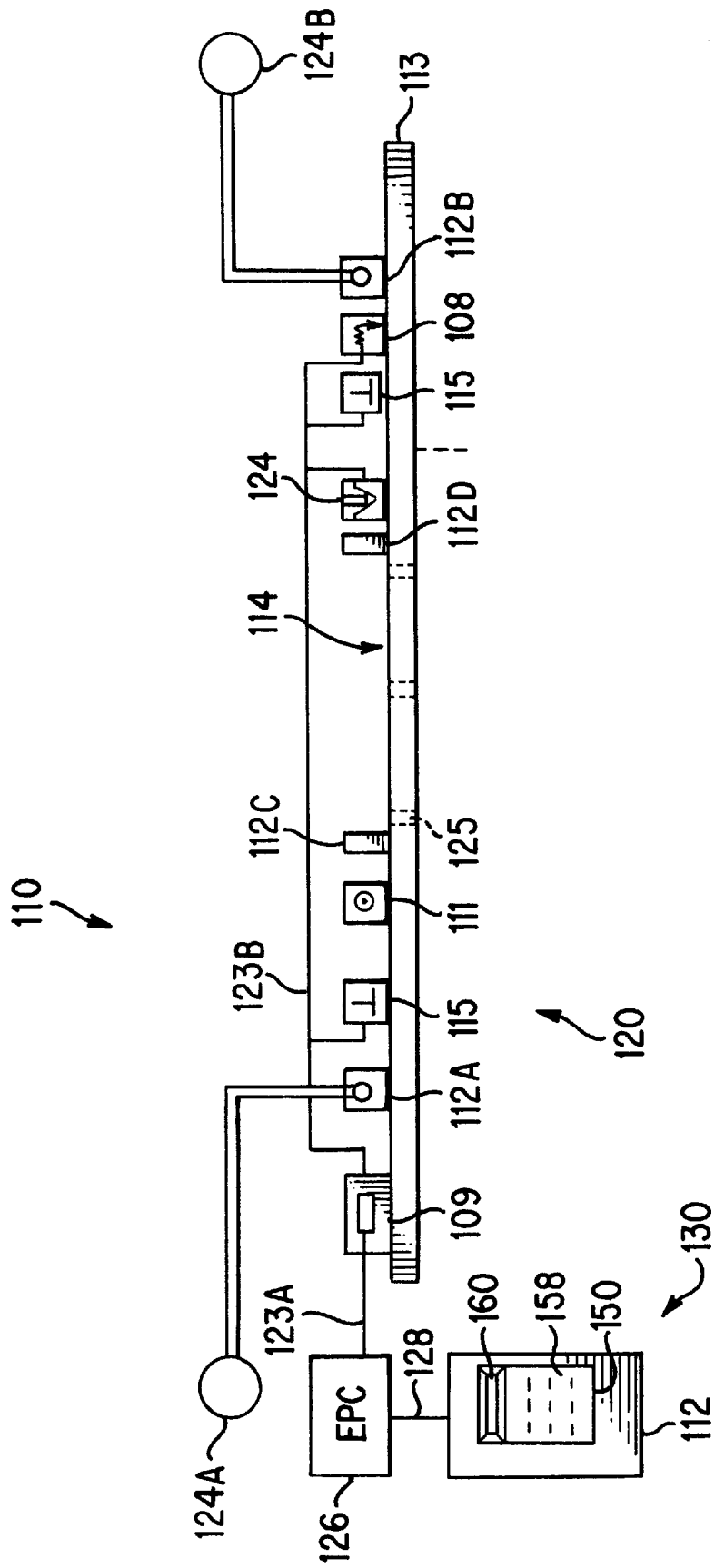
FIG. 1 is a simplified block diagram of an analytical instrument constructed to include a planar manifold assembly and a novel fluid connector system for use therein in accordance with the present invention.

An analytical instrument is shown in FIG. 1 and is generally designated as chromatograph 110 having a planar manifold assembly 120 and a control section 130. The planar manifold assembly 120 is provided in a compact configuration such that, in comparison to a conventional gas chromatograph, the planar manifold assembly 120 occupies less volume, has a smaller footprint, is amenable to configuration as a portable unit, is less complex and costly to manufacture, and consumes less operating power.

In order to perform a chromatographic separation of a given sample compound, a sample is injected into the planar manifold assembly 120 with a pressurized carrier gas by means of a sample inlet 111. The carrier gas supplied to inlet 111 is provided from a source 124A through one or more fluid connectors 112A into a planar manifold 113, which incorporates internal channels capable of bearing fluid flow, each of which serve in part to control or redirect a plurality of gas flows. The detector gases are provided from respective sources (one such source 112B is shown) through respective fluid connectors 112B to the planar manifold 113. A separation column (not shown) may be attached to a portion of the planar manifold 113 at its inlet and outlet ends to selected channels 125 in the planar manifold 113 by respective fluid connectors 112C, 112D. The carrier gas/sample combination passing through column is exposed to a temperature profile by known means. During this profile of changing temperatures, the sample will separate into its components primarily due to differences in the interaction of each component with the column 114 at a given temperature. As the separated components exit the column, they are detected by a detector 124.

In a first feature of the present invention, some of the fluid-handling functional devices in the planar manifold assembly 120 are contemplated as being surface-mounted to the planar manifold 113 and others are mounted to upright fluid connectors. The contemplated fluid-handling functional devices include passive devices such as the aforementioned inlet 111 and fluid connectors 112A, 112B, 112C, 112D; active devices such as valves 115, regulators (not shown in FIG. 1), and the like; and signal generating devices such as sensors 108, detector 124, and so on. The active devices and the signal generating devices are contemplated as being operated under control signals generated by the control section 130 on data and control lines 123A, 123B, and 128 connected to computer 122 and pneumatic controller 126. Accordingly, the computer 122, pneumatic controller 126, and planar manifold 113 may be operated to effect a variety of fluid handling functions. The planar manifold assembly 110 preferably includes one or more electronic signal connectors 109 and associated cabling (shown in simplified form as line 123B for clarity) for control, data, and power signals as may be needed. It is contemplated that for some applications an optional interface in the form of an electronic control panel 150 having a keypad 158 and a display 160 may be included.

Turning now to FIGS. 2–5, a preferred embodiment of a planar manifold 210 contemplated by the present invention includes a front plate 210A having front side 210C and a back plate 210B having back side 210D; these plates are sized and constructed to be superimposed and bonded together during the manufacturing process to form the planar manifold 210. Preferably, the front plate 210A and back plate 210B are machined from nickel-plated stainless steel and etched to provide an arrangement of etched channels 210E each capable of sustaining fluid flow. That is, the etched channels 210E form a predetermined array of internal channels when the front plate 210A and back plate 210B are bonded together to form the planar manifold 210.

In contrast to the conventional approach, wherein the task of forming complex interconnected flow paths usually involves the use of many discrete pieces of tubing and fittings through which the pieces of tubing can be attached, the planar manifold 210 replaces conventional manifolds at a fraction of the cost and with minimal labor. Further details on the design and manufacturing of a planar manifold having etched channels therein may be found in commonly-assigned U.S. Pat. No. 5,567,868, issued to Craig et. al., the disclosure of which is included herein by reference.

The planar manifold 210 is robust, rigid, shock proof, and unaffected by operation in a high temperature environment. Hence, the planar manifold 210 is intended as a primary structural support member of the embodiment 200, in addition to serving as a pneumatic flow manifold for managing a complex arrangement of fluid flows.

It is contemplated that certain ones of the etched channels such as channels 203A, 210E in one or both of the front and back plates 210A, 210B are connected via appropriate fluid connectors constructed according to the present invention to certain fluid-handling functional devices. Description of the fluid connectors with respect to suitable upright fluid handling functional devices will be now described with reference to FIG. 2A; a description of the fluid connectors with respect to surface-mounted fluid handling functional devices will be described with reference to FIG. 2B.

Figure 2A:
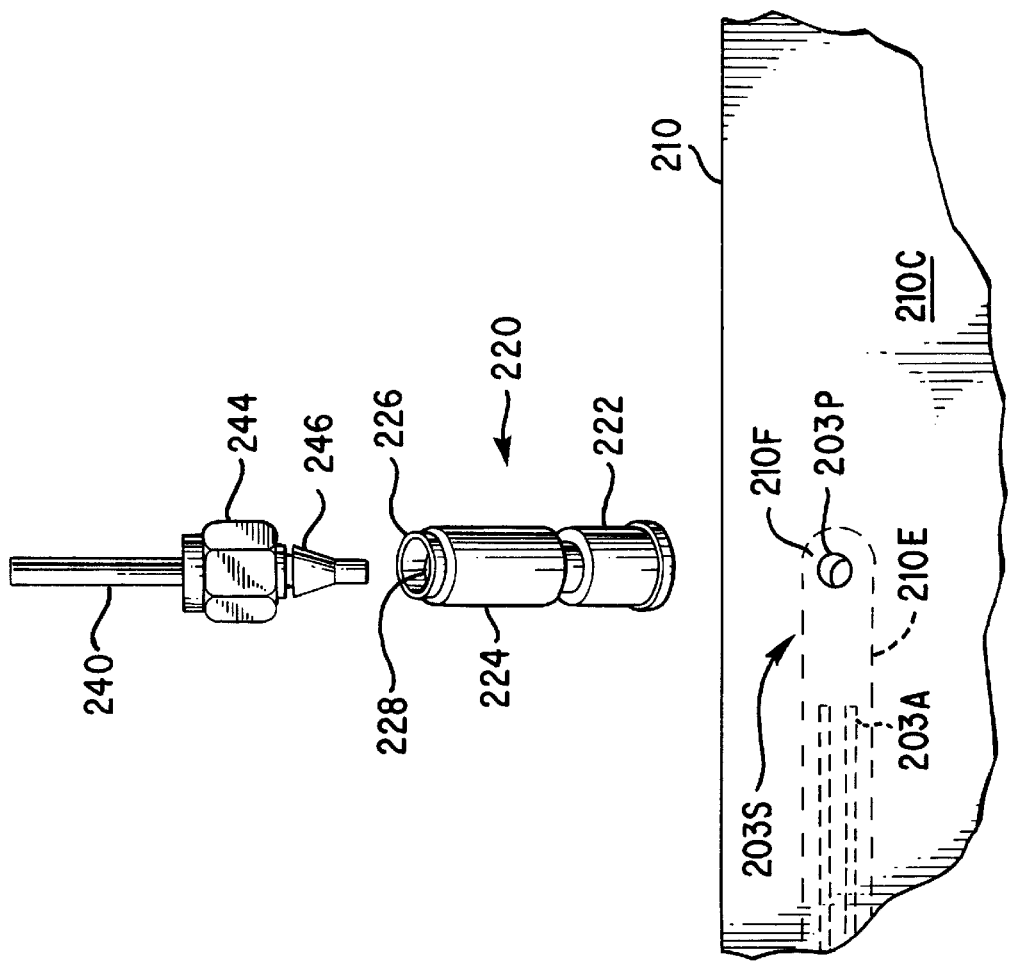
FIG. 2A is side perspective view of a portion of the planar manifold assembly of FIG. 1, illustrating an embodiment of the invention for connecting tubular fluid-handling functional devices to the planar manifold assembly, in exploded view with certain components of the planar chromatographic assembly being omitted for clarity.
Figure 3B:
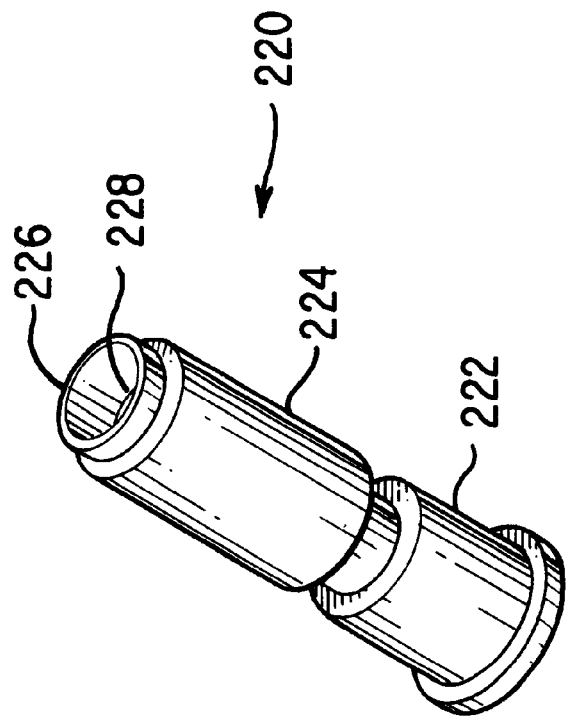
FIG. 3A and 3B are side perspective views of a preferred embodiment of a fluid connector shown in FIG. 2A.
Figure 3A:
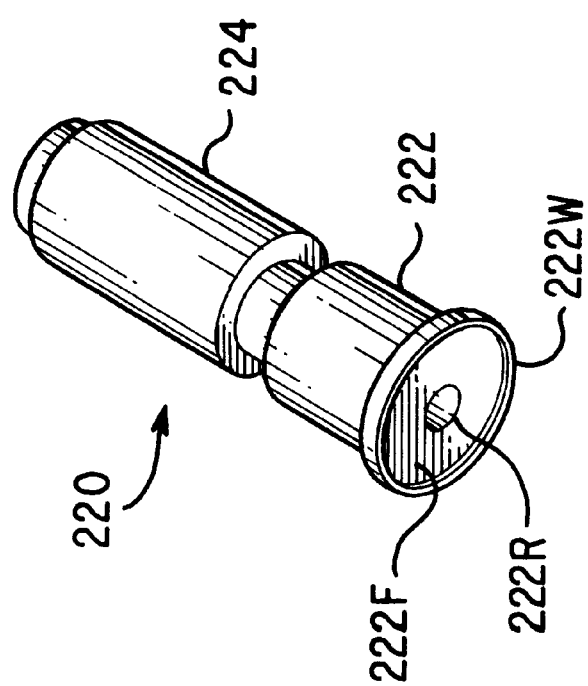
Figure 5B:
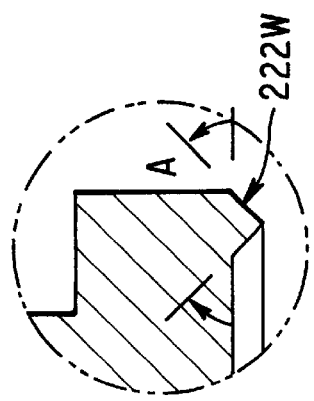
FIG. 5B illustrates a weld projection integrated into a circumferential edge portion of the fluid connector shown in FIG. 2A, in detailed view for clarity.
Figure 5A:
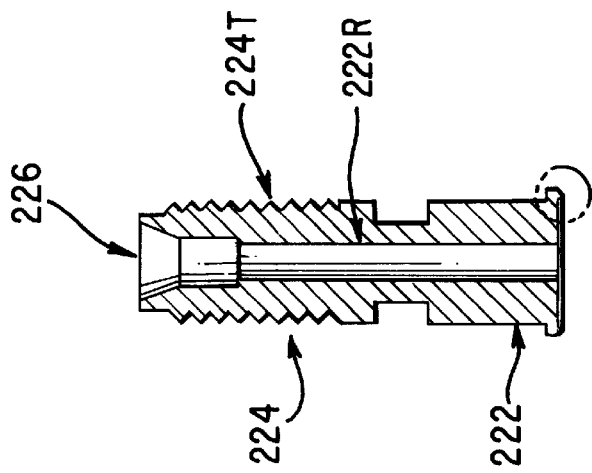
FIG. 5A is a simplified cross-sectional view of the fluid connector shown in FIG. 2A
Figure 4A:
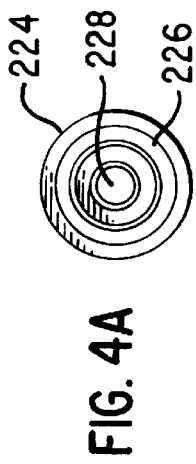
FIGS. 4A–4C are top, side, and bottom views of the fluid connector shown in FIG. 2A.
Figure 4B:
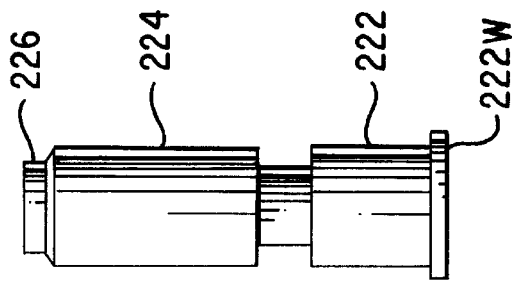
Figure 4C:
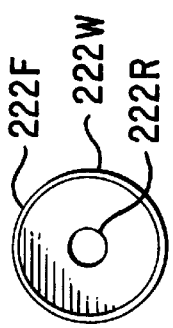
Figure 9:
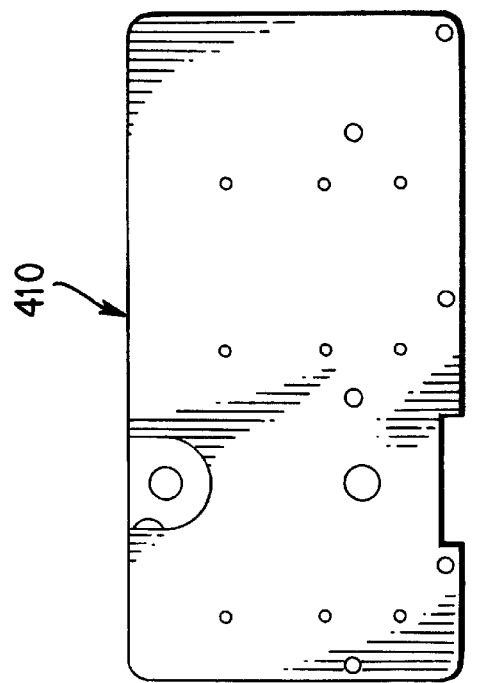
FIGS. 8, 9, 10, and 11 are top, bottom, side, and perspective views, respectively, of another embodiment of a planar manifold assembly constructed according to the present invention to include the flu deconnectors of FIGS. 4–5 and the surface-mounted fluid handling functional device of FIGS. 6–7.
Figure 8:
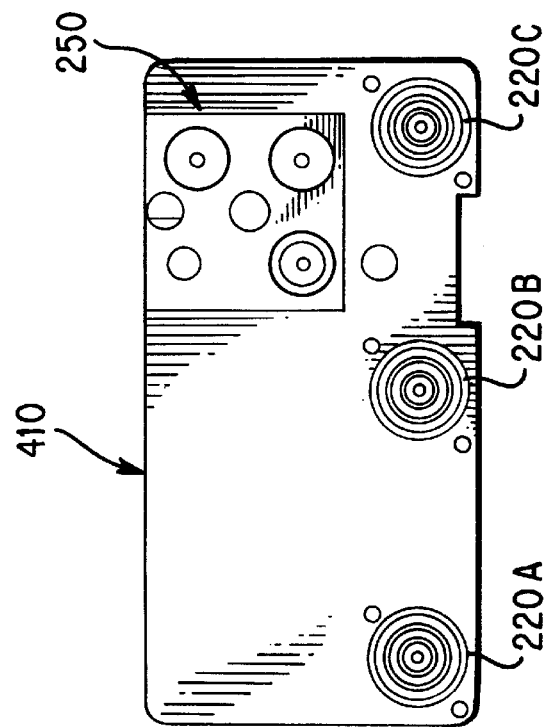
Figure 11:
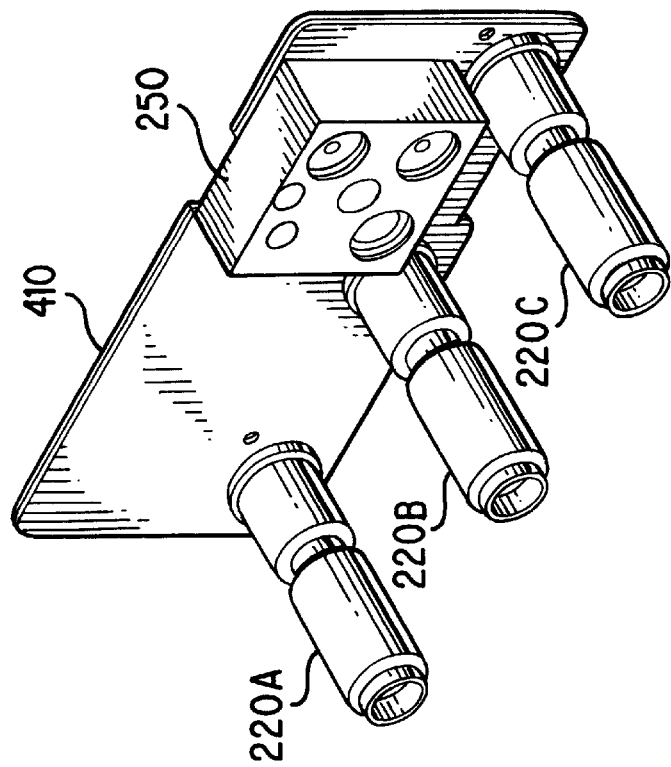
Figure 10:
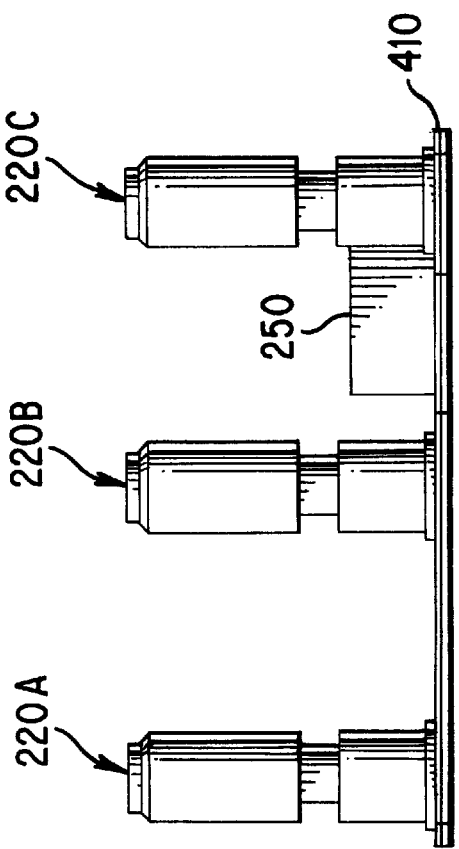

As illustrated in FIG. 2A and 3A–3B, located on the front side 210C are certain ones of the etched channels 210E that may be directed to respective ones of the manifold port surface regions 203S each having a port 203P suitable for effecting fluid communication with complementary ports in an upright-mounted fluid-handling functional device 220. In particular, the etched channels 210E extend to the portion of the planar manifold 210 (preferably in the immediate vicinity of the port 203P) where an interface surface 210F is located for receiving the respective weld projection 334, 344, 346.

A preferred embodiment of an upright fluid connector 220 may be constructed for connecting a channel 210E in the planar manifold 210 to an upright fluid handling functional device such as a tube 240. The upright fluid connector 220 is constructed to include generally cylindrical upper and lower fittings 222, 224. Impressing the upright fluid connector 220 onto the manifold 210 superimposes an interface surface 222F on an interface surface 210F on the planar manifold 210. A bore 222R is superimposed over the port 203P. The bore 222R effects fluid communication between the internal bore of the tubing 240 to the port 203P and hence to the etched channel 210E. It is important to insure integrity and freedom from leakage in the fluid communication between the tube 240, upright fluid connector 220, and interface surfaces 222F and 210F. Accordingly, a projection weld 222W encompasses the interface surface 222F and bore 222R such that the fluid connector 220 may be subject to resistive welding onto the prepared interface surface 210F. By effecting a pulsed application of electrical current flow between the fluid connector 220 and the interface 210F on the planar manifold 210C, the weld projection 222W is subject to high current density and is fused to the interface surface 210F. The upright fluid connector 222 is thereby fixed to the planar manifold 210 and, simultaneously, a hermetic seal is effected between the interface surfaces 210F, 222F. Accordingly, the bore 222R is unified in hermetically-sealed fluid communication with the port 203P.

Sufficient overlap of the two interface surfaces 210F and 204F allows the location of the connector 204B to be adjusted if necessary with respect to the opening of the etched channel 210E. Preferably, the upper fitting 224 includes means for sealing the gap between the exterior of the tube 240 and a port 228. The attachment means includes a receiver 226 at the port 228 on the major axis of the upper fitting 224 such that the port 228 can perpendicularly engage a complementary retention means such as a nut 244 on the tube 240. A sealing means such as a ferrule 246 is provided for reversible fluid connection with the receiver 226. As the nut 244 engages threads, snap locks, or similar engagement means (not shown) on the upper fitting 224, the ferrule 246 is compressed to effect the desired seal. Alternatively, the attachment, sealing, and engagement means may be omitted, the threaded section on the fluid connector may be omitted, and the tube 240 may be attached via brazing the tube 240 to the receiver 226. Alternately, the braze could be omitted and the tube exterior may be prepared with a ductile surface material, or a high temperature ceramic cement, such that forced insertion of the tube 240 is sufficient to provide a gas-tight seal at the receiver 226.

Figure 2B:
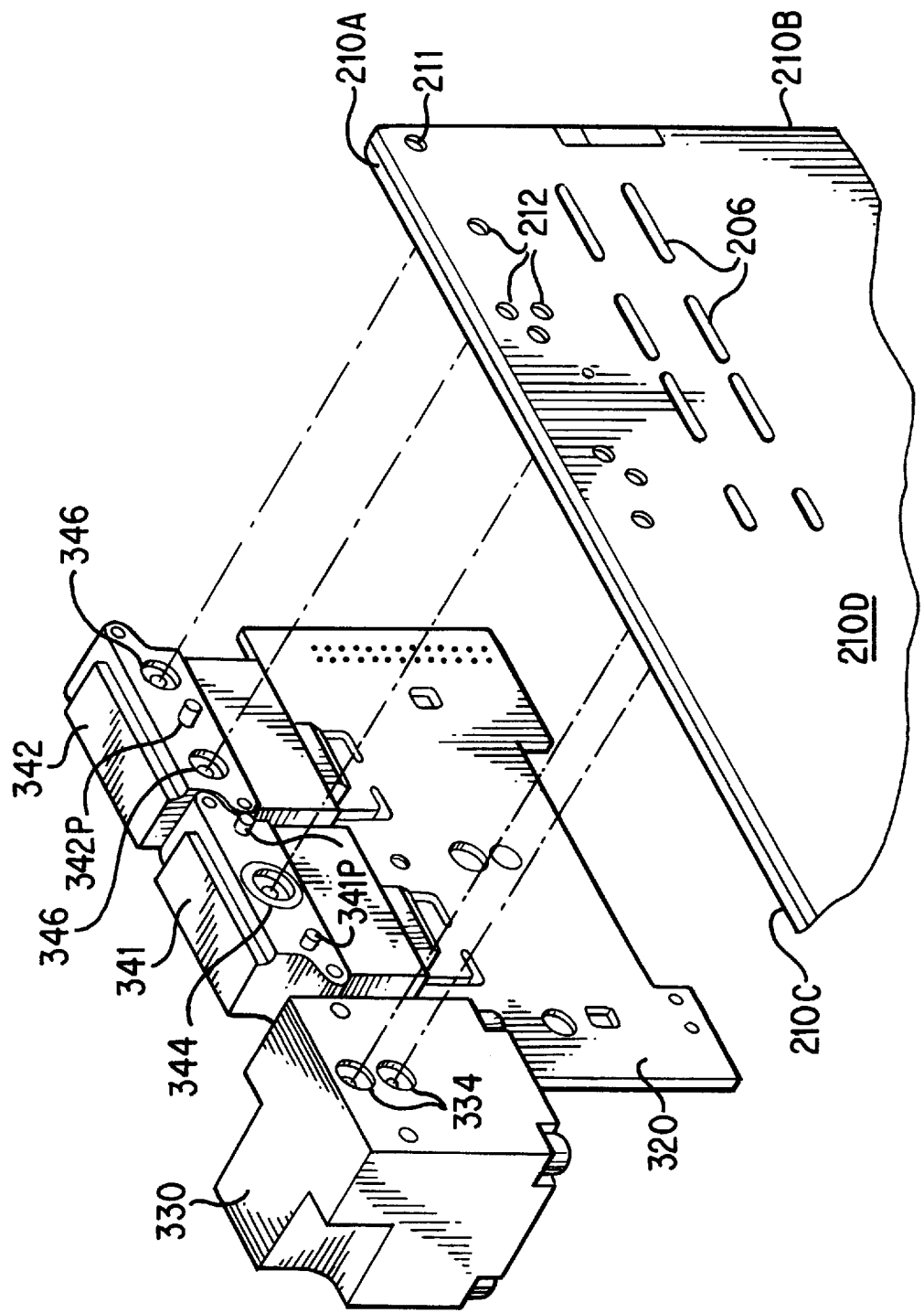
FIG. 2 is a side perspective view of a another portion of the planar manifold assembly of FIG. 2A, illustrating an embodiment of the invention for connecting surface-mounted fluid-handling functional devices to the planar manifold assembly, in exploded view for clarity.

As shown in FIG. 2B, another preferred embodiment of a fluid connector may be employed for effecting a hermetic seal between selected surface-mounting fluid-handling functional devices and a corresponding one of the etched channels 210E. For example, a flow controller 330 may be constructed as a purge flow controller; and a first sensor 341 may be constructed as a pressure sensor and a second sensor 342 may be constructed as a flow sensor. Ports on the fluid-handling functional devices include a circular weld projection (such as weld projection 334 on purge flow controller 330, weld projection 344 on first sensor 341, and weld projection 346 on second sensor 342) for sealing the device to the planar manifold 210.

The planar manifold 210 can include a variety of other physical features for accommodating certain mechanical functions, such as to accommodate a fluid connector or cabling for one or more data and control signal interface boards 320. Stand-offs consisting of simple posts may be mounted to the portions of the planar manifold 210 on which a separation column is positioned. Oblong openings 206 are distributed longitudinally to effect a thermal break between the perimeter of the planar manifold 210 and the interior portions. Locator holes are provided for locating and aligning components; for example, corner holes 211 are provided for locating the planar manifold 210 on respective protrusions (not shown); through-holes 212 allow passage of the protrusions 341P, 342P used to precisely locate sensors 341, 342 with respect to manifold ports, and so on.

As shown in FIGS. 6–11, a fitting block 250 may be constructed for various purposes, such as to transfer gas from a supply line and provide fluid communication to one or more of the etched channels in another embodiment of a planar manifold 410. The supply line (not shown) attaches to a first surface 251 in the fitting block 250 so as to transfer a flow of carrier gas from a passageway 254 into a port 261P in the second surface 252 in the fitting block 250. The fitting block 250 may also include an internal frit (not shown). The fitting block 250 is constructed to include other fluid-bearing passageways such as passageway 256. Each additional port 262P and 264P are also provided with weld projections 262, 264. The preferred angle A defined by the surfaces of the weld projections 261 is approximately ninety degrees, although other angles are contemplated. Plural fluid connectors 220A, 220B, 220C may be included as well.

Figure 12B:
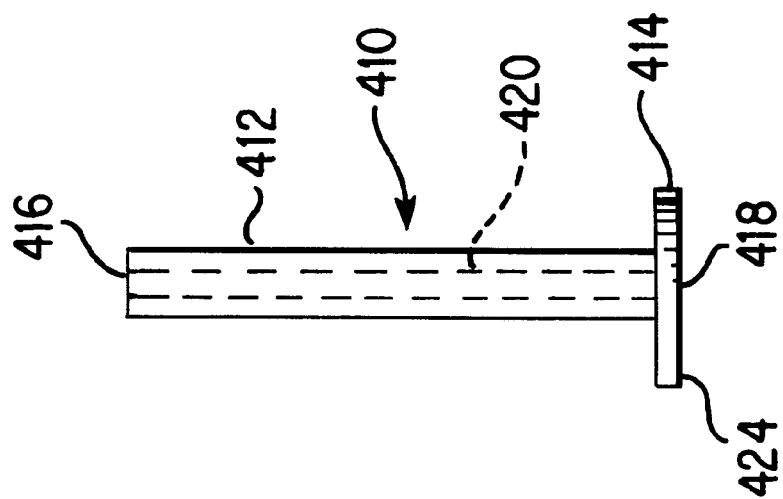
FIGS. 12A and 12B illustrate side perspective and side elevation views of an embodiment of an upright fluid handling functional device constructed according to the present invention.
Figure 12A:
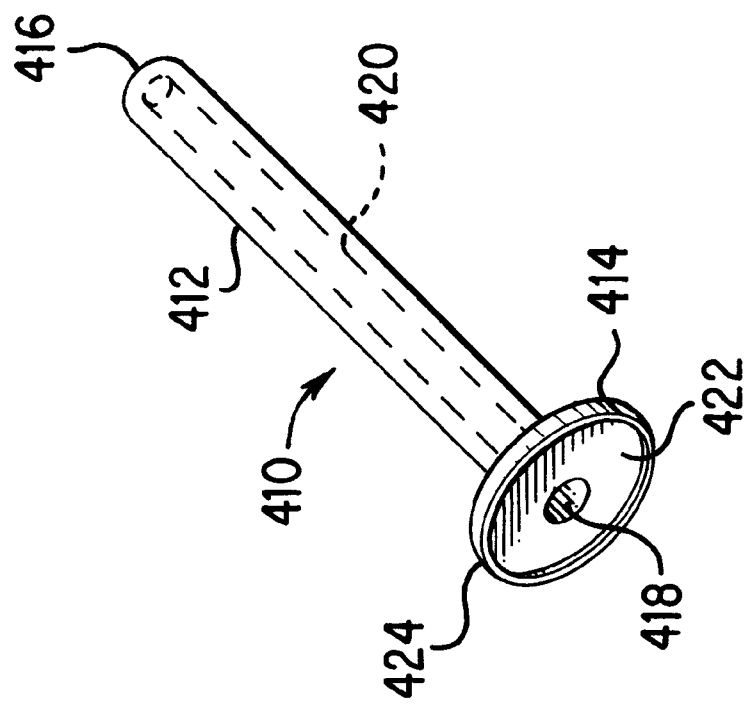

FIGS. 12A and 12B illustrate side perspective and side views of another embodiment of an upright fluid connector for use with an upright fluid handling functional device. The upright fluid connector 410 is well-suited for connecting narrow-bore tubing, such as capillary tubing, to a planar manifold. The upright fluid connector 410 includes a upper fitting 412 shaped as a tube stub and an attached lower fitting 414 shaped as a disk-like platform. The upper fitting extends from a center portion of the lower fitting 414. At opposing ends of the connector 410 are upper and lower ports 416, 418. An internal bore 420 provides fluid communication between the upper and lower ports 416, 418. The lower port 418 is located in an planar interface 422 from which a weld projection 424 extends. The weld projection 424 encircles the lower port 418. Upon resistive welding, the weld projection 424 and the resulting line of contact are merged, thus fixing the interface 422 to the planar manifold.

Use of the illustrated embodiments of fluid connectors in a planar manifold assembly afford the following benefits and advantages: a compact configuration; a reduction in the use of conventional fluid connections, which would otherwise undesirably increase the overall volume of the planar manifold assembly; reliable fluid connections between fluid-handling functional devices (such as fittings, valves, sensors, and the like) and a plurality of flow paths in the planar manifold; greater use of miniaturized fluid-handling functional devices that otherwise are difficult to connect to the planar manifold; greater use of miniaturized fluid-handling functional devices which can advantageously be constructed to be either upright-mounted or surface-mounted configurations, so as to allow a very compact assembly and yet also offer reliable, fluid-tight connection without the complexity and difficulty of conventional fluid connectors; a reduction in the high cost and complexity exhibited by conventional connectors.

A large number of fluid-handling functional paths may thus be integrated into a compact, low-profile form factor in a fashion that heretofore would be difficult if not impossible to assemble using traditional tubular pipe, ferrules, and manual fittings. Also, considerable cost savings and improved reliability are realized by reduction of the number of connections necessary to achieve multiple flow paths.

The surface-mounted pneumatic connections provided by the invention also reduce the complexity of the planar manifold assembly, which is desirable during the stages of manufacturing, assembly, repair, or modification of the analytical instrument in which the planar manifold assembly may be situated.

Another advantage is that the planar manifold assembly may be constructed to use certain conventional fluid-handling devices, such as a capillary separation column, that otherwise are difficult to connect to a planar receiving surface, thus saving cost and providing for simpler manufacturing.

While the invention has been described and illustrated with reference to specific embodiments, those skilled in the art will recognize that modification and variations may be made without departing from the principles of the invention as described herein above and set forth in the following claims.

What is claimed is:

1. A fluid connector system for connecting a conduit having a fluid-bearing capability to a channel located in a planar manifold assembly and having a fluid-bearing capability, comprising:

a fluid connector having a first port surface region and a first port therein, the first port being adapted for fluid communication with the conduit;

a receiver section in the planar manifold assembly having the channel located therein and a second port surface region having a second port therein, the second port being in fluid communication with the channel; and a weld projection located in at least one of the first and second port regions, the weld projection encircling a respective one of the first and second ports;

wherein the first and second ports regions may be urged together to cause a line of contact between the weld projection and the opposing one of the first and second port surface regions, and wherein the weld projection and the first and second port regions being adapted for receiving an electrical current therebetween to cause resistive heating of the weld projection and the line of contact, whereby the weld projection is fused to the opposing one of the first and second port surface regions, and whereby a hermetic seal is obtained around the juncture of the superimposed first and second ports.

2. The system of claim 1, wherein the weld projection is provided in an annular form.

3. A fluid connector for effecting leak-free transfer of a fluid between a conduit and a channel in a planar manifold, the planar manifold having a receiver section and the channel located therein, and manifold port surface region having a manifold port therein, the manifold port being in fluid communication with the channel, comprising:

an upper fitting shaped as a tube stub;

a lower fitting attached to the upper fitting, the upper fitting extending from a center portion of a topside of the lower fitting, and the lower fitting being shaped as a disk-like platform;

a lower port at the underside of the platform;

an upper port at the mouth of the tube stub;

an internal bore providing fluid communication between the upper and lower ports;

a downwardly-extending weld projection encircling the lower port;

whereby the weld projection is adapted for resistive heating and fusion with the manifold port surface region upon being urged against the manifold port surface region while the manifold port and the lower port are superimposed, and upon application of a current pulse therebetween, so as to fix the underside of the platform to the planar manifold such that a hermetic seal is obtained around the juncture of the superimposed lower port and manifold port.

4. The connector of claim 3, wherein the weld projection is provided in an annular form.

5. A fluid connector for effecting leak-free transfer of a fluid between an open end of a conduit and a channel in a planar manifold, the planar manifold having a receiver section and the channel located therein, and manifold port surface region having a manifold port therein, the manifold port being in fluid communication with the channel, comprising:

a rigid body having upper and lower fittings;

a cavity in the upper fitting for receiving the open end of the conduit;

a central bore extending between an upper port in the cavity and a lower port in the underside of the lower fitting, the bore providing fluid communication between the upper and lower ports;

a downwardly extending weld projection encircling the lower port;

whereby the weld projection is adapted for resistive heating and fusion with the manifold port surface region upon being urged against the manifold port surface region while the manifold port and the lower port are superimposed and upon application of a current pulse therebetween, so as to fix the underside of the platform to the planar manifold such that a hermetic seal is obtained around the juncture of the superimposed lower port and manifold port.

6. The connector of claim 5, wherein the weld projection is provided in an annular form.

7. A method for connecting a first port in a conduit having a first port surface region to a second port in a channel located in a planar manifold assembly, the channel having a second port surface region, and at least one of the first port and the second port being encircled by a weld projection extending from the respective first or second port surface regions, comprising the steps of:

(A) mounting the first port surface region onto the second port surface region to engage the leading edge of the weld projection against the opposing port surface region, (B) superimposing the first and second ports;

(C) urging the first port surface region and the second port surface region together to cause a line contact between the leading edge of the the weld projection and the opposing one of the first and second port surface regions; and (D) subjecting the first and second port surface regions to a period of current flow therebetween sufficient to cause localized resistive heating of the leading edge of the projection weld and at the line of contact that is sufficient to melt and fuse the weld projection and the opposing port surface region at the line of contact, whereby a hermetic seal is obtained around the juncture of the first and second ports.

* * * * *